United States Patent [19]

Lixl et al.

[11] Patent Number: 4,921,425
[45] Date of Patent: May 1, 1990

[54] MODEL OPERATING INSTRUMENT FOR UPPER JAW OSTEOTOMY

[76] Inventors: Georg Lixl, Untereching 72, A-5110 Oberndorf; Christian Krenkel, Moosstrasse 126, A-5020 Salzburg, both of Austria

[21] Appl. No.: 186,931
[22] Filed: Apr. 27, 1988
[51] Int. Cl.$^5$ ............................................. A61C 11/00
[52] U.S. Cl. ........................................ 433/62; 433/63
[58] Field of Search .................. 433/61, 62, 63, 64, 433/65, 55, 56

[56] References Cited

U.S. PATENT DOCUMENTS

| | | | |
|---|---|---|---|
| 4,352,663 | 10/1982 | Lee | 433/56 |
| 4,391,589 | 7/1983 | Monfredo et al. | 433/63 |
| 4,402,670 | 9/1983 | Lee | 433/61 |

FOREIGN PATENT DOCUMENTS 386333 1/1988 Austria .

Primary Examiner—John J. Wilson
Assistant Examiner—Adriene J. Lepiane
Attorney, Agent, or Firm—Lorusso & Loud

[57] ABSTRACT

The invention describes a model operating instrument for upper jaw osteotomy, with a basic frame on which it is possible to adjust the position of the two temporo-maxillary articular cups; from the side, there protrudes into the osteotomy plane a universally mounted disc which is rotatable in its own plane and which is displaceable in three directions at right-angles to one another, on which disc it is possible to fix an upper jaw model keyed with a lower jaw model.

3 Claims, 4 Drawing Sheets

MODEL OPERATING INSTRUMENT FOR UPPER JAW OSTEOTOMY

FIELD OF THE INVENTION

The invention relates to a model operating instrument for upper jaw osteotomy, comprising a basic frame on which it is possible to adjust the position of the two temporo-maxillary articulator cups.

BACKGROUND OF THE INVENTION

In dental engineering, articulators are normally used in which an upper jaw part is mounted in that the articulator cups constructed thereon are placed on vertical pegs rigid with the instrument and having spherical top ends. In their size and spacing, these pegs correspond substantially to the articulator heads, thus defining a horizontal pivot axis corresponding to the hinging axis of the temporo-maxillary joint.

Such articulators can only be used to a limited extent in performing model operations in the jaw area. In fact, it is vital to such model operations to establish whether an envisaged operative measure is leading to the desired improved occlusion of the upper and lower rows of teeth without adversely affecting the function of the temporo-maxillary joints. To this end, the best procedure is to join to each other the models produced of the upper jaw and lower jaw in the desired position of occlusion and then to check which changes in the joint area would result from such a connection. The next step is to establish which operative measures (while retaining the desired improved occlusion) would restore normal conditions in the area of the joint.

Carrying out the program which has been outlined is not possible with a conventional articulator, since with such an instrument, the interior of the articulator cups is inaccessible by reason of the articulator heads which serve for mounting the hinging axis. The description of Austrian Application A 212/87 has, however, already disclosed a way of making the area representing the articulator cups accessible from below. If the articulator cups are made from transparent material, for example acrylic glass, then it is readily possible to observe the relative movement between the articulator heads of the lower jaw model and of the fossa during pivoting of the upper jaw part of the articulator and so assess the reliability of an intended operative measure. In the initial stage of the model operation in which even greater deflections of the articulator heads of the model of the lower jaw from the desired position take place, it is not sufficient to make the articulator cups accessible from below; instead, deviations of the articulator heads upwardly must also be temporarily acceptable. This is made possible in that the temporo-maxillary joint cups are represented by a frame-like sighting area in which an arrangement of cross hairs consisting of flexible threads or the tip of a measuring rod define the desired position of the articulator heads.

The arrangement according to Austrian Published Specification A 212/87 has already proven successful for model operations in respect of the lower jaw. In this case, two-piece jaw angle templates are used, the plane of separation between the two parts corresponding to the division which takes place in sagittal lower jaw osteotomy. The two parts are shifted in respect of each other until the desired occlusion is achieved while maintaining an anatomically and physiologically viable position of the articulator heads of the lower jaw in the articulator cups.

SUMMARY OF THE INVENTION

The object of the invention is to be able to establish also in supramaxillary osteotomy the consequences of a three-dimensional displacement of the bone sections through the maxillary antrums and nasal walls for the reciprocal location of articulator heads and cups of the lower jaw. According to the invention, it is envisaged that a universally mounted disc rotatable in its own plane and adapted for displacement in three directions at rightangles to one another be projected into the osteotomy plane from the side, a model of the upper jaw keyed to a model of the lower jaw being capable of being fixed on the said disc.

Preferably, in order to register variations in the initial position of the disc, a measuring plate should be insertable from the side and having passing through it at least three measuring needles which rest on the disc.

The arrangement according to the invention makes it possible for the operating surgeon to establish by which combination of measures on the upper and/or lower jaw it is possible to achieve the required occlusion without adversely affecting the functioning of the joint. Should these measures prove to be too radical, the instrument makes it possible to determine the optimum compromise between operative measures and attainable occlusion.

BRIEF DESCRIPTION OF THE DRAWING

Details of the invention are set out hereinafter with reference to the accompanying drawings, in which.

DETAILED DESCRIPTION OF THE PREFERRED EMBODIMENT

Figure 1:
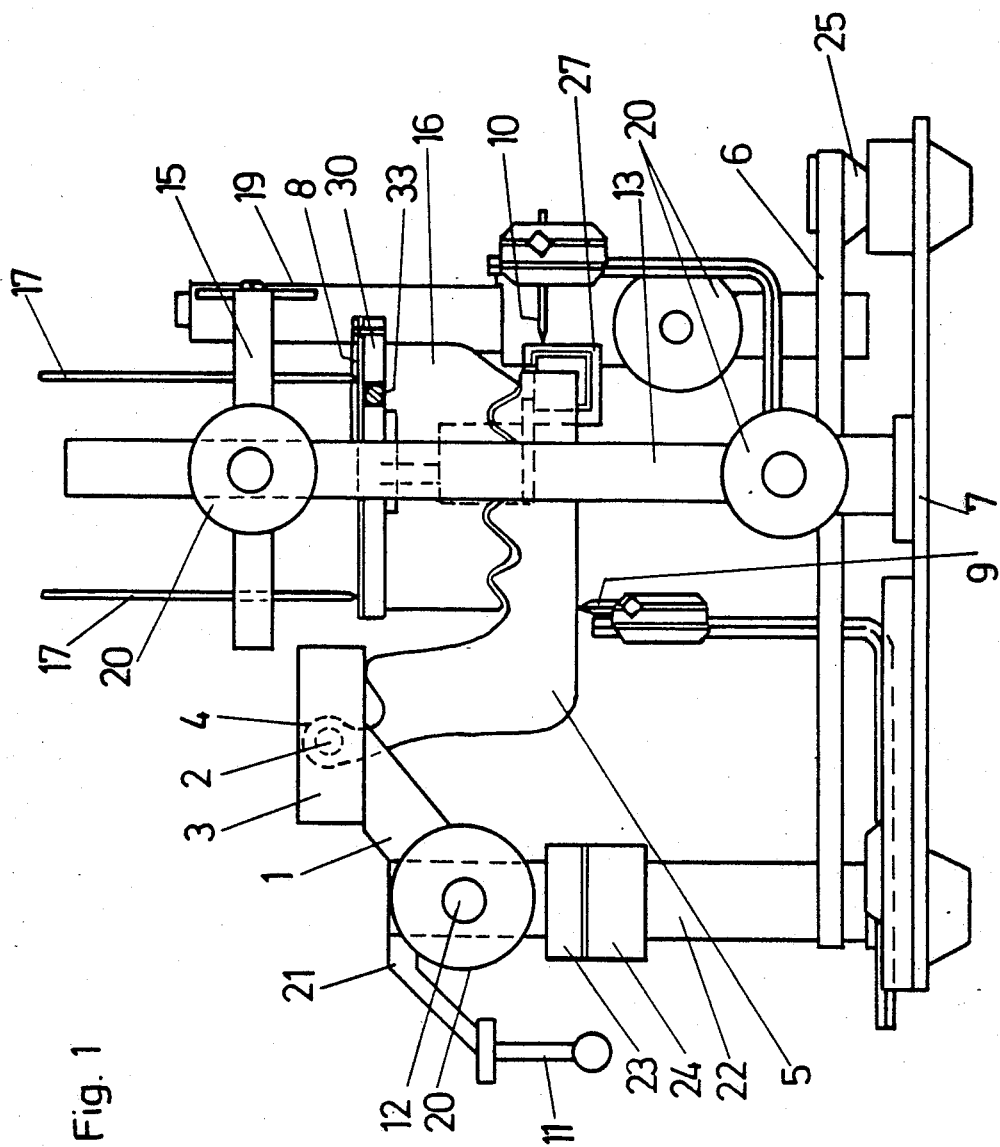
FIG. 1 shows a model operation instrument (with keyed upper and lower jaw model) viewed from the side.
Figure 2:
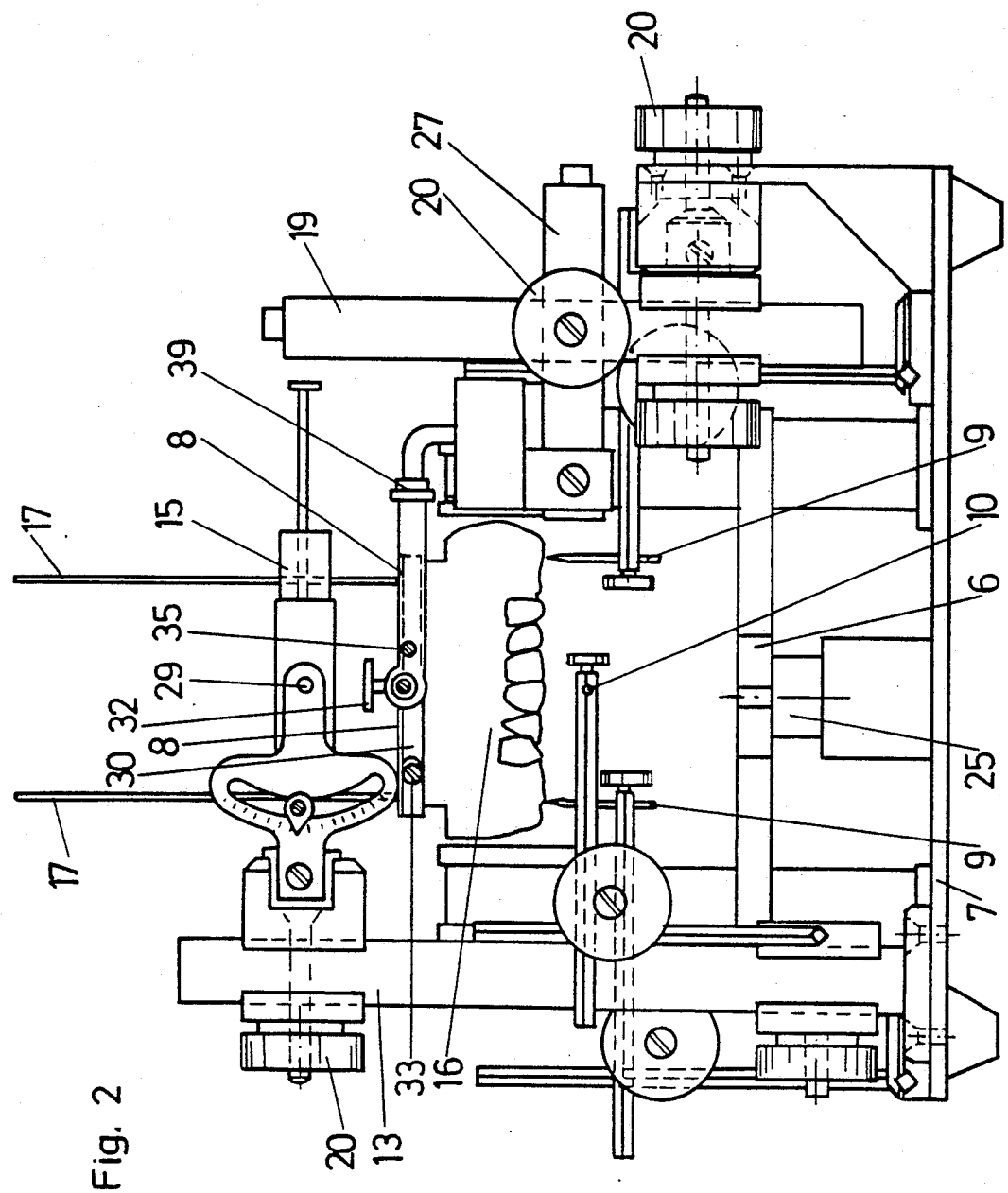
FIG. 2 (with upper jaw model) from the front.

The basic frame in which, in the present case, it is possible to adjust the position of the temporo-maxillary joint cups, consists of a base plate 6 which carries columns 22, the height of which can be varied by a sleeve 23 provided with an indexing pin, and a locking nut 24. Mounted on the columns 22 by means of a spindle 12 is a turret 21 which makes it possible to pivot hinge journals 11 forward instead of sighting panels 3 mounted on the bearing bracket 1 by means of a spindle 2, so that the basic frame can also be used as a conventional articulator. So that the description shall not be unnecessarily complicated, this possibility will not be referred to again hereinafter.

Figure 3:
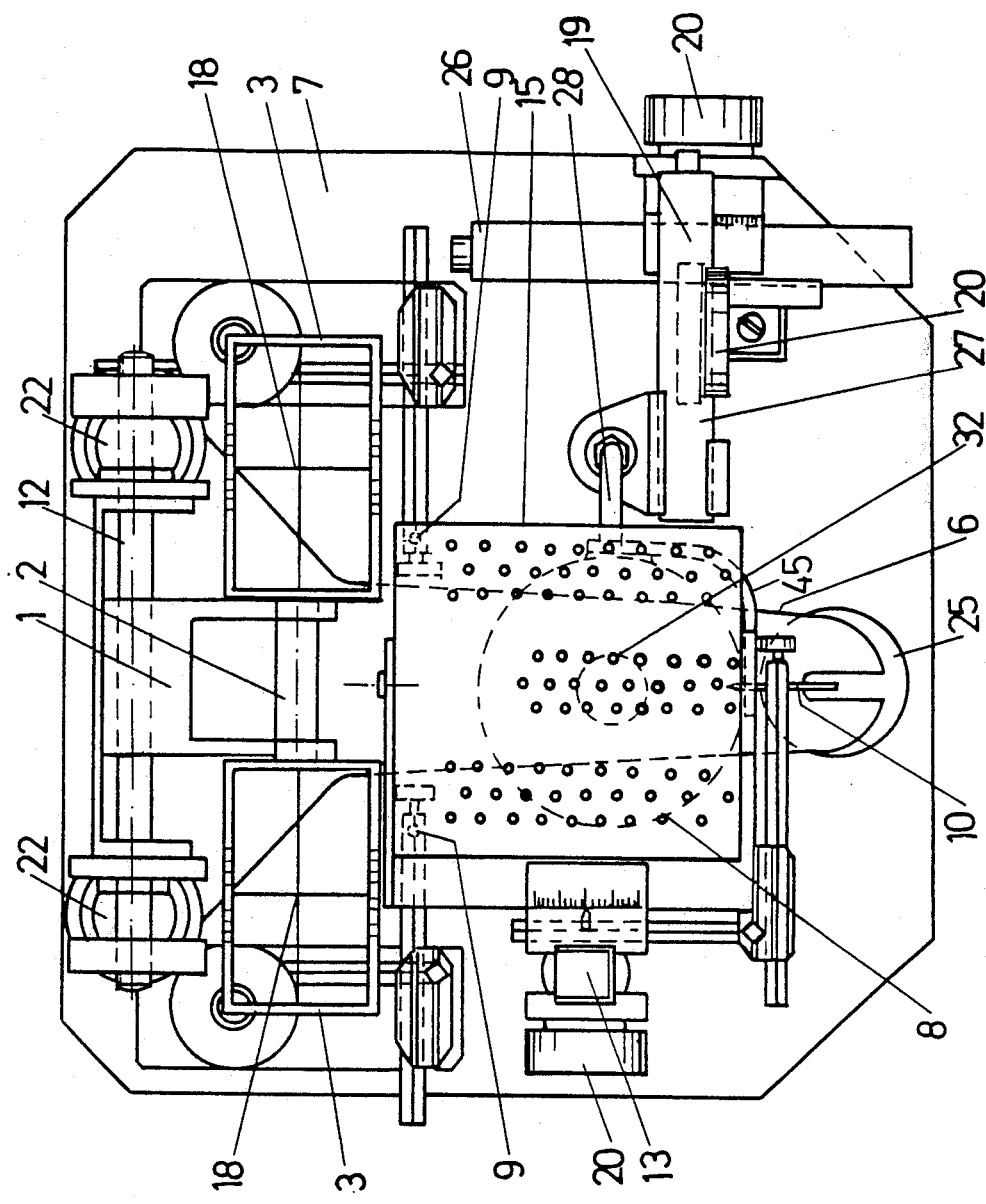
FIG. 3 a model operation instrument from above.

The cross hairs 18 in the sighting panels 3 which can be seen in FIG. 3 define the desired position of the articulator heads 4 of the lower jaw model 5. Since the cross hairs 18 consist of rubber threads, they permit deviations of the articulator heads 4 from the desired position during the initial phase of the model operation.

To be able to perform model operations of the upper jaw, the basic frame described, which stores the position of the temporomaxillary joint cups and thus defines the desired position of the articulator heads, is connected to a frame 7 by a screwed joint 25. On its left-hand side, when viewed from the front, the frame 7 carries a holder for a measuring plate 15 which consists of perforated acrylic glass. This holder consists essentially of a column 13 to which the plate 15 is secured by a milled screw 20. This plate can be pivoted about an axis 29 to a measurable degree. The purpose of it is to establish by means of measuring needles 17 any changes in the position of the disc 8 which constitutes the essential element of the invention.

The disc 8 which carries the upper jaw model 16 (usually keyed with the lower jaw model 5) is fixed on the supporting rod 28 via a support arm 45 in a manner described in greater detail hereinafter. This supporting rod 28 is mounted on a cross bar 27 and is displaceable in a lateral direction and together with this in a longitudinal direction on a longitudinal bar 26. The longitudinal and cross bars are adjustable in height along a column 19.

Within the framework of the invention, less important measuring pins 9 and 10 make it possible to register the position of the underside of the of the front of the lower jaw model 5.

Figure 4:
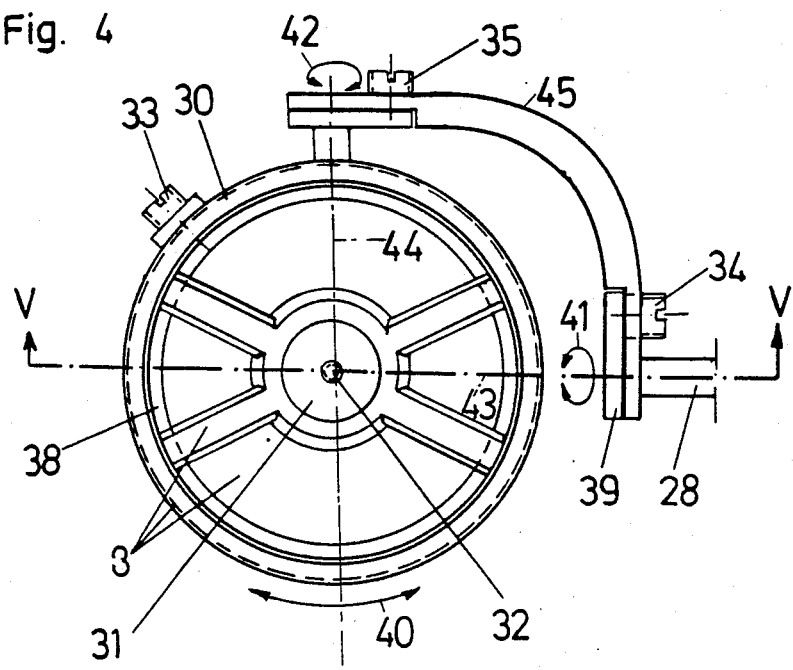
FIG. 4 and 5 show the universally mounted disc from below and in cross-section.
Figure 5:
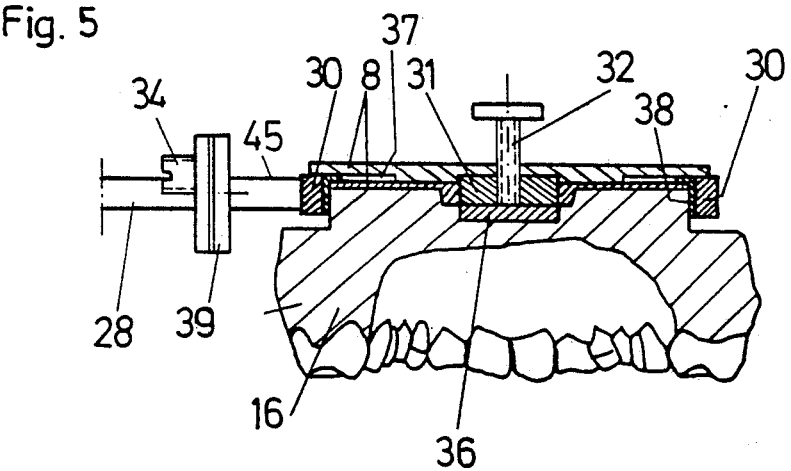

The disc 8 which is essential to the invention, and also the way it is mounted, are shown more precisely in FIGS. 4 and 5. The disc 8 comprises an encircling groove 37 into which a flange 38 of an annular frame 30 engages. The disc 8 is fixed in the frame 30 by means of the screw 33.

The disc 8 connected to the frame 30 can be rotated as represented by double-arrow 40, in respect thereof about its vertical central axis. In addition, there is opportunity for rotation about the axis 43 of the supporting rod 28, as represented by double-arrow 41 and the position attained can be locked by means of the screw 34. Rotation about a horizontal axis 44 normal thereto is likewise possible as represented by double-arrow 42. Locking is once again possible by means of the screw 35.

Fitting the upper jaw model 16 on the disc 8 is usually carried out by what is referred to as the quick-split method. For this purpose, there is disposed in the disc 8 a magnet 31 which co-operates with a magnetizable inlay 36 in the upper jaw model 16. A screw 32 which traverses a screwthread in the magnet 31 makes it possible carefully to separate the parts 31 and 36 from each other.

What is claimed is:

1. A model operating instrument for measuring the effects of upper jaw osteotomy on the temporo-maxillary joints of a model jaw assembly having articulator heads, said instrument comprising: a basic frame having means for adjustably defining and storing the position of two temporo-maxillary joint cups and thus the desired position of the articulator heads of a lower jaw model; and a disc, horizontally mounted on the basic frame for location in the osteotomy plane of the upper jaw, rotatable in its own plane and adapted for displacement in three directions at right-angles to one another, said disc being universally mounted so as to be rotatable about two horizontal axes which are perpendicular to one another and which intersect the center of the disc, a model of the upper jaw keyed to a model of the lower jaw being capable of being fixed on said disc.

2. The model operating instrument according to claim 1, further comprising a measuring plate vertically adjustable and insertable from the side to a position above the disc, said measuring plate being able to rotate, to a measurable degree, about a horizontal axis intersecting, the center of the measuring plate and being traversed by at least three measuring needles which rest on the disc so that changes in the position of the disc from its starting position can be measured.

3. The model instrument according to claim 1, wherein the means for adjustably defining and storing the position of the two temporo-maxillary joint cups comprises a transparent sighting panel having transparent cross hairs so that variations in the initial position of the articulator heads of the jaw assembly in respect of the fixed temporo-maxillary joint cups which occur as the result of displacement of the disc are rendered visible.

* * * * *